United States Patent
Jutras et al.

(10) Patent No.: US 6,996,487 B2
(45) Date of Patent: Feb. 7, 2006

(54) AUTOMATIC CALIBRATION SYSTEM FOR COMPUTER-AIDED SURGICAL INSTRUMENTS

(75) Inventors: Sébastien Jutras, Montréal (CA); Éric Brosseau, Montréal (CA); Herbert André Jansen, Montréal (CA); Gabriel Côté, Outremont (CA); Louis-Philippe Amiot, Hampstead (CA)

(73) Assignee: Orthosoft Inc., Montréal (CA)

(*) Notice: Subject to any disclaimer, the term of this patent is extended or adjusted under 35 U.S.C. 154(b) by 360 days.

(21) Appl. No.: 10/220,303

(22) PCT Filed: Mar. 15, 2001

(86) PCT No.: PCT/CA01/00326
§ 371 (c)(1),
(2), (4) Date: Sep. 13, 2002

(87) PCT Pub. No.: WO01/67979
PCT Pub. Date: Sep. 20, 2001

(65) Prior Publication Data
US 2003/0040879 A1  Feb. 27, 2003

(51) Int. Cl.
*A61B 5/05* (2006.01)

(52) U.S. Cl. ..................... 702/107; 600/414
(58) Field of Classification Search .......... 702/107, 702/150, 152; 600/104, 117, 411, 414, 423; 606/1
See application file for complete search history.

(56) References Cited

U.S. PATENT DOCUMENTS

| | | | |
|---|---|---|---|
| 5,617,857 A | * | 4/1997 | Chader et al. ............ 600/424 |
| 5,921,992 A | | 7/1999 | Costales et al. |
| 6,021,343 A | | 2/2000 | Foley et al. |
| 6,112,113 A | * | 8/2000 | Van Der Brug et al. ..... 600/427 |
| 6,306,126 B1 | * | 10/2001 | Moctezuma ................. 606/1 |
| 6,434,507 B1 | * | 8/2002 | Clayton et al. ............ 702/152 |
| 6,470,207 B1 | * | 10/2002 | Simon et al. .............. 600/426 |
| 6,497,134 B1 | * | 12/2002 | Faul et al. ................ 73/1.81 |
| 6,511,418 B2 | * | 1/2003 | Shahidi et al. ............ 600/117 |
| 6,662,036 B2 | * | 12/2003 | Cosman ................... 600/411 |
| 6,675,040 B1 | * | 1/2004 | Cosman ................... 600/427 |
| 2004/0073279 A1 | * | 4/2004 | Malackowski et al. ....... 607/88 |

FOREIGN PATENT DOCUMENTS

| | | |
|---|---|---|
| DE | 196 39 815 A1 | 4/1998 |
| EP | 0 986 991 A1 | 3/2000 |
| WO | WO 97/29710 | 8/1997 |
| WO | WO 99/01078 | 1/1999 |

OTHER PUBLICATIONS

U.S. Appl. No. 60/193,209.*

* cited by examiner

*Primary Examiner*—Carol S. W. Tsai
(74) *Attorney, Agent, or Firm*—Ogilvy Renault LLP

(57) ABSTRACT

A system for automatic calibration of instruments (S) having varying cross-sectional dimensions within a predetermined range and having detectable elements (110, 112, 113, 114) thereon for computer-aided surgery, comprising a calibration base (C) having detectable elements (43, 44, 46, 48) secured thereto for detecting a position and an orientation thereof in space by sensors (204) connected to a position calculator (202). The calibration base is adapted to receive and to releasably secure a working shaft (100) of any of the instruments (S) and provides an abutting surface (14) for a tip (102) thereof in such a way that a position and orientation of the tip (102) of the instrument (S) secured therein is calculable when working shaft cross-section dimensions thereof are known. The position calculator (202) receives instrument data (214) and calibration data (218) from an operator through a user interface (206) and stores the instrument data (214) and calibration data (218) for subsequent calibrations.

29 Claims, 4 Drawing Sheets

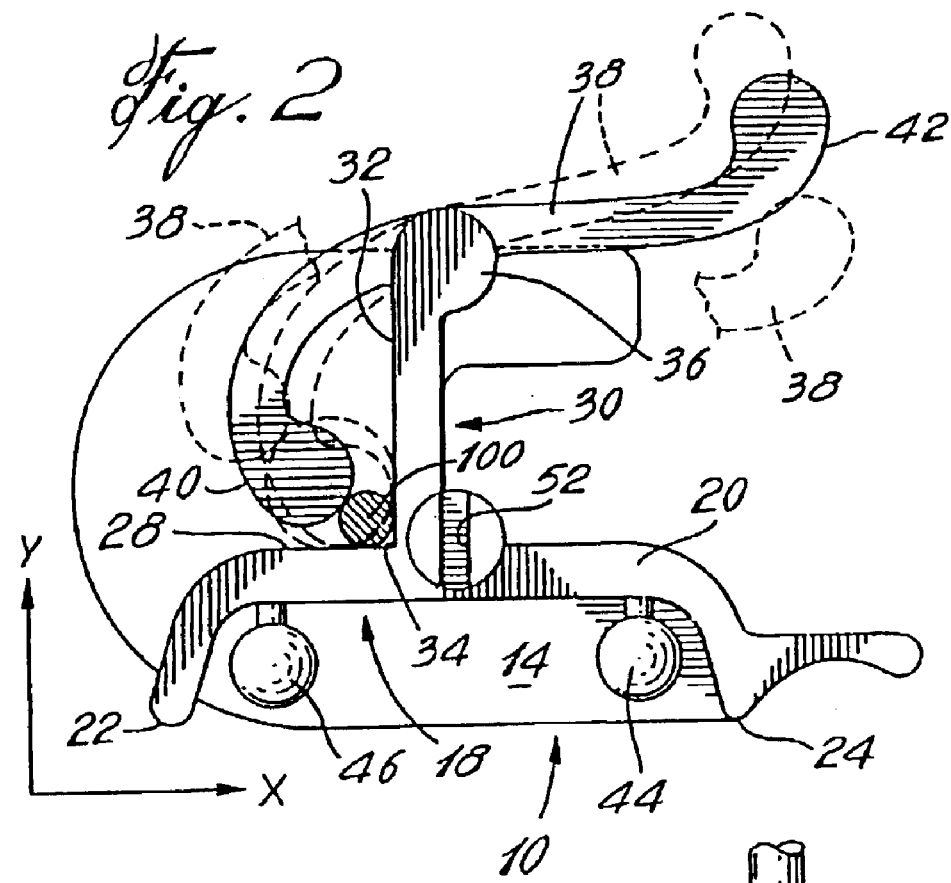
Fig. 2
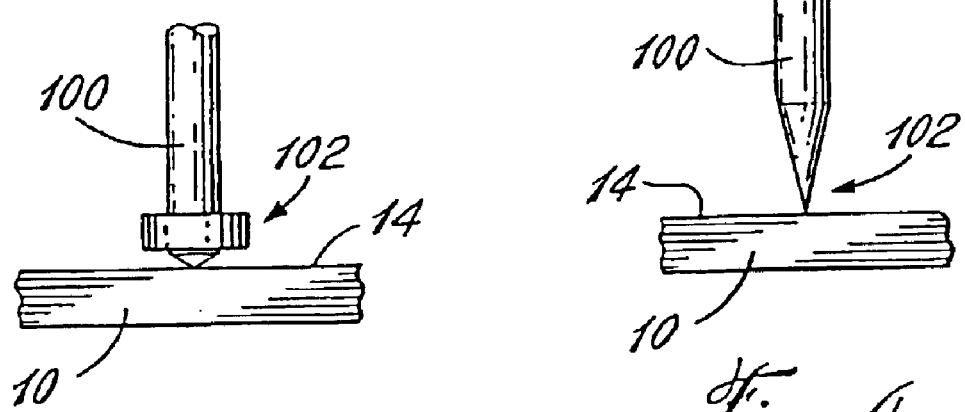
Fig. 3
Fig. 4
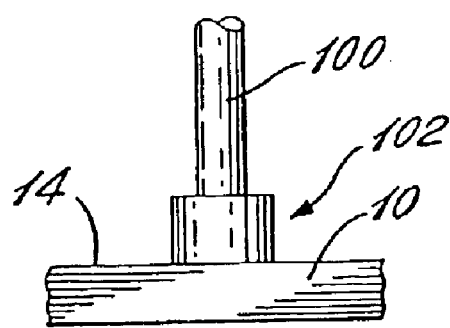
Fig. 5

AUTOMATIC CALIBRATION SYSTEM FOR COMPUTER-AIDED SURGICAL INSTRUMENTS

BACKGROUND OF THE INVENTION

1. Field of the Invention

The present invention relates to computer-aided surgery instrumentation and, more particularly, to the calibration thereof.

2. Description of the Prior Art

In computer-aided surgery, it is known to use surgical instruments detectable by positioning systems in order to have an on-screen representation of the instrument with respect to an operated part of a patient's body. It is readily understood that great amounts of precision and accuracy are required in the space positioning of the surgical instruments in order to obtain reliable representation of the operation. A misrepresentation of the instrument with respect to the patient's body may have dramatic consequences and may even be fatal to the patient. Thus, prior to computer-aided surgery, the instruments must be calibrated.

One known method of calibrating is referred to as the axial-conical calibration. This method consists in achieving pre-determined maneuvers with a surgical instrument having detectable devices thereon for it to be located in space by sensors connected to a position calculator. Namely, a first maneuver consists in rotating the surgical instrument with respect to its longitudinal axis, whereby the position of the latter is set. During this rotation, the position calculator receives readings which will allow it to calculate a transform matrix from the positioning system to the axis of the instrument. Thereafter, in a second maneuver, the instrument is rotated according to a conical trajectory having as an apex the working tip thereof. Hence, the positioning system may interpret and find another transform matrix between the positioning system and the tip of the surgical instrument. Although the axial-conical calibration method is simple, the required maneuvers of calibration may take a few minutes to an inexperienced user and the position calculator may require to repeat the maneuvers if they are judged as being unsatisfactory.

Calibration systems having permanently calibrated instruments have been provided in order to avoid lengthy steps of calibration. In such systems, a working field is scanned by sensors connected to a position calculator which recognizes the geometry of a given surgical instrument, whereby it is calibrated.

Precautions must be taken when using permanently calibrated instruments to ensure that these are not altered or damaged, whether it be in pre-surgery sterilization or during surgery. The instruments are subject to frequent manipulations during surgery, and thus, having sensors or detectable devices thereon involves the possibility that the position of these sensors or detectable devices is altered, whereby precision is lost in the space representation of the instrument. In this case, an inventory of equivalent instruments must be on hand during surgery in case of damage or alteration to an instrument. It would thus be desirable to have a calibration system allowing frequent calibrating by its simplicity and its rapidity of execution, to better suit the surgical room environment.

SUMMARY OF THE INVENTION

It is an aim of the present invention to provide a method for automatically calibrating surgical instruments which is simple and rapid in use and which produces a calibration of constant precision to facilitate the calibrating.

It is a further aim of the present invention to provide a method for automatically calibrating surgical instruments which includes validating the calibration.

It is a still further aim of the present invention to provide an apparatus for automatically calibrating surgical instruments which accommodates a wide range of instruments.

It is a still further aim of the present invention to provide an apparatus for automatically calibrating surgical instruments and capable of sustaining sterilization.

Therefore in accordance with the present invention, there is provided a calibration base to automatically calibrate instruments having varying cross-sectional dimensions within a predetermined range for computer-aided surgery. Each of the instruments has detectable means, a working shaft and a tip at an end of the working shaft. The calibration base comprises detectable means secured thereto for detecting a position and an orientation thereof in space by sensors connected to a position calculator. The calibration base is adapted to receive and to releasably secure the working shaft of any of the instruments. The calibration base provides a first abutting surface for the tip thereof in such a way that a position and orientation of the tip of any of the instruments secured therein is calculable when working shaft cross-section dimensions thereof are known, whereby any of the instruments is calibrated when the position of the tip of the working shaft thereof is calculated.

Also in accordance with the present invention, there is provided a method for calibrating the above described calibration base. The method comprises the steps of (i) detecting a position and orientation in space of the detectable means of the calibration base and of the instrument by the sensors, (ii) receiving instrument data including either identification data relating to instrument cross-sectional dimension data stored by the position calculator or of instrument cross-sectional dimension data to be stored by the position calculator for subsequent calibrations, and (iii) calculating a position of a tip of any one of the instruments secured in the calibration base with respect to the detectable means of the calibration base whereby the instrument is calibrated with respect to the detectable means of the instrument.

Further in accordance with the present invention, there is provided a system for automatic calibration of instruments for computer-aided surgery. The system comprises a calibration base as described above. Sensors detect a position and orientation in space of the detectable means of the calibration base and of the instrument. The position calculator as described above is connected to the sensors for calculating a position and orientation of the tip of the working shaft of the instruments secured in the calibration base with respect to the detectable means thereon whereby any of the instruments is calibrated with respect to the detectable means on the instrument when the position of the tip of the working shaft thereof is calculated.

BRIEF DESCRIPTION OF THE DRAWINGS

Having thus generally described the nature of the invention, reference will now be made to the accompanying drawings, showing by way of illustration a preferred embodiment thereof, and in which:

FIG. 2 is a top plan view, partially cross-sectioned, of the automatic calibration unit with an optically detectable tool;

FIG. 3 is a fragmented side elevational view of an example of an instrument tip disposed on the automatic calibration unit;

FIG. 4 is a fragmented side elevational view of another example of an instrument tip on the automatic calibration unit;

FIG. 5 is a fragmented side elevational view of a further example of an instrument tip on the automatic calibration unit;

DESCRIPTION OF THE PREFERRED EMBODIMENTS

Figure 1:
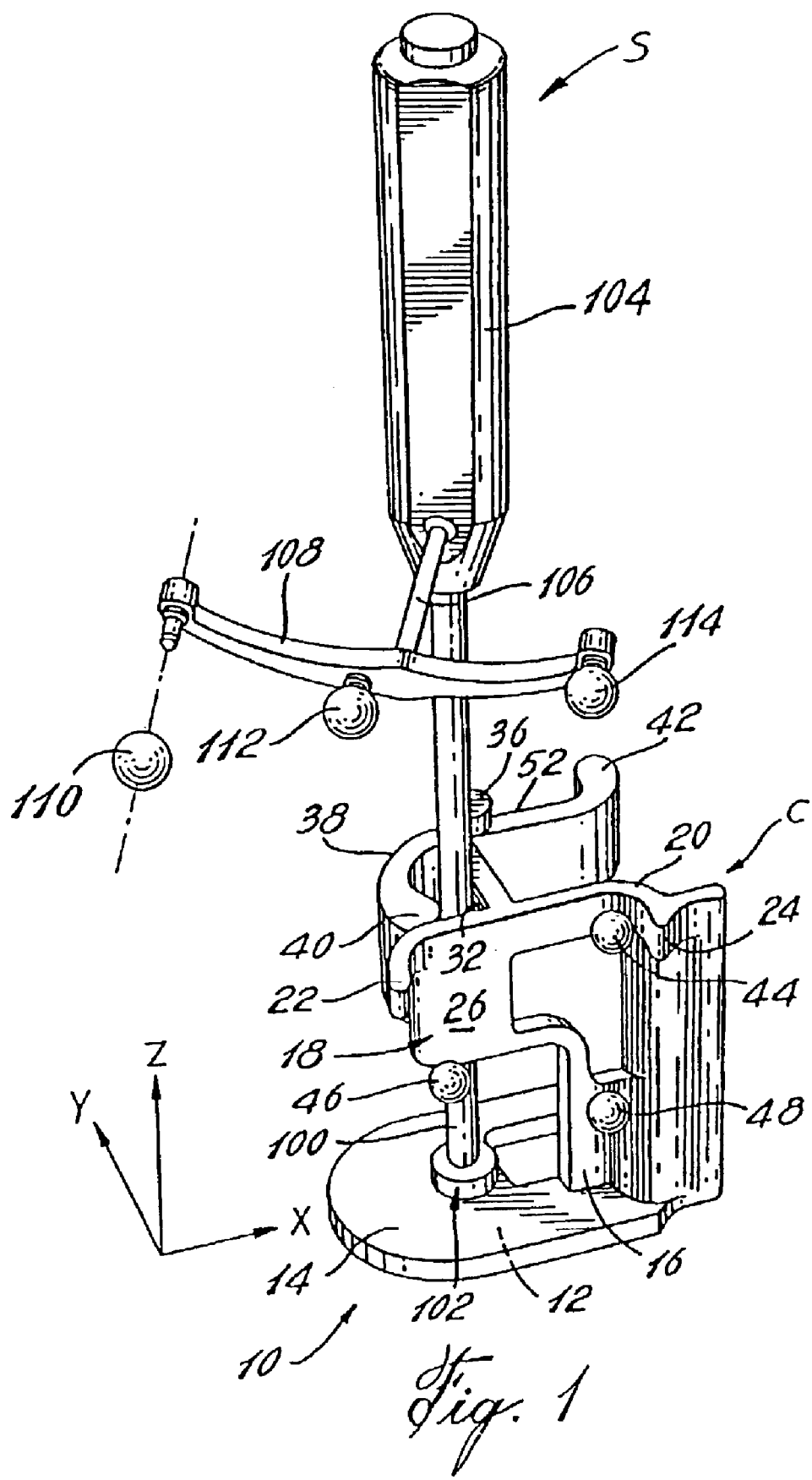
FIG. 1 is a perspective view of an automatic calibration unit with a tool in accordance with the present invention.

Referring to FIG. 1, there is shown a calibration base C supporting a surgical instrument S. The calibration base C comprises a base plate 10 having a bottom flat surface 12. The base plate 10 also defines an XY plane 14. For clarity purposes, XYZ axes have been added to the drawings in order to clearly identify the space orientation of planar elements. For instance, the XY plane 14 is planar with respect to the XY axes provided therewith. Also, it is noted that the calibration base C generally consists in a material which must be able to sustain several cycles of autoclave sterilization, such as a stainless steel. Some elements of the calibration base C will require to be made of other materials and will be identified herein as such.

A vertical wall 16 extends perpendicularly from the XY plane 14 of the base plate 10. A first panel 18 projects from a top portion of the vertical wall 16 and shares a top edge surface 20 therewith. A first protrusion 22 and a second protrusion 24 protrude from a proximal surface 26 of the vertical wall 16 and of the first panel 18, and are adjacent the top edge surface 20 thereof.

As best seen in FIG. 2, the first panel 18 defines an XZ plane 28 on the back of the proximal surface 26. The XZ plane 28 is perpendicular with respect to the XY plane 14. Referring now to both FIGS. 1 and 2, a second panel 30 is shown extending perpendicularly from the XZ plane 28 of the first panel 18, and thereby defines a YZ plane 32. The YZ plane is perpendicular with the XZ plane 28, and thus with the XY plane 14. The XZ plane 28 and YZ plane 32 intersect at an edge line 34.

As best seen in FIG. 2, a top bulge 36 and a bottom bulge (not shown) extend horizontally (i.e. in the XY plane) from the top and bottom of the second panel 30, with a lever 38 pivotally disposed therebetween. The lever 38 has rounded ends 40 and 42 at its extremities. A spring (e.g. torsion spring) is shared between the lever 38 and the second panel 30 such that the lever 38 is biased toward the edge line 34 at the intersection of the XZ plane 28 and the YZ plane 32. The lever consists in a material able to sustain the high-pressure of an autoclave during the sterilizing of the calibration base C, such as an acetal copolymer.

Returning to FIG. 1, detectable spheres 44, 46 and 48 are secured to the proximal surface 26 of the vertical wall 16 and the first panel 18. The detectable spheres are coated with a retro-reflective layer in order to be detected by, for instance, an infrared sensor using axial illumination. It is pointed out that other shapes are known and could also be used as alternative embodiments to retro-reflective spheres. As an example, straight cylinders, corner reflectors or the like having retro-reflective properties could also be used. It is also noted that the detectable spheres 44, 46 and 48 may be removed by providing snap-fit mating adapters such that single-use spheres may be used. This allows for the spheres to be sterilized with processes milder than autoclave sterilization, whereby a coating does not need to be characterized by its capability to sustain high temperatures or pressures.

Still referring to FIG. 1, the surgical instrument S is shown having a shaft 100 of circular cross-section. A tip 102 is disposed at a working end thereof, whereas a handle 104 is disposed at a handling end thereof. Referring to FIGS. 3, 4 and 5, tips of various tools in accordance with the present invention are shown at 102. Returning to FIG. 1, an arm 106 extends from the handle 104 of the surgical instrument S. A blade 108 is disposed at a free end of the arm 106 and comprises detectable spheres 110, 112 and 114 secured thereto. The detectable spheres 110, 112 and 114 are similar in construction to the above mentioned detectable spheres 44, 46 and 48.

The calibration base C is adapted for receiving and releasably securing surgical instruments having working shafts of a wide range of cross-section shapes and diameters (e.g. 3 to 37 mm). In the preferred embodiment, instruments having circular cross-sections are used with the calibration base C. As seen in FIG. 2, the surgical instrument S is abutted against the XZ plane 28 and the YZ plane 32 and is biased in this position by the lever 38. By knowing the diameter of the working shaft 100, it is possible to calculate the positioning of the longitudinal axis thereof (i.e. at the center of the circular cross-section) which is possible with respect to the edge of the calibration base C. Moreover, the surgical instrument S is disposed in the calibration base C with the working tip 102 thereof touching the XY plane 14 of the base plate 10.

As the position and orientation of the detectable spheres 44, 46 and 48 may be determined by sensors, and the position of these spheres on the calibration base C is known as they are secured thereto, the position and orientation of the working tip 102 of the surgical instrument S is calculable as it is located at the intersection of the longitudinal axis of the working shaft 100 and the XY plane 14 of the calibration base C.

Although the preferred embodiment discloses planes 14, 28 and 32 all being in a perpendicular relation, it is pointed that the planes 14, 28 and 32 may be in any relation with respect one to another so long as the position of a given portion of the instruments is calculable. For instance, the planes 28 and 32 may define a V-shaped channel of obtuse or acute angles for receiving the working shaft 100 thereagainst, even though the preferred embodiment discloses a right angle therebetween.

Figure 6:
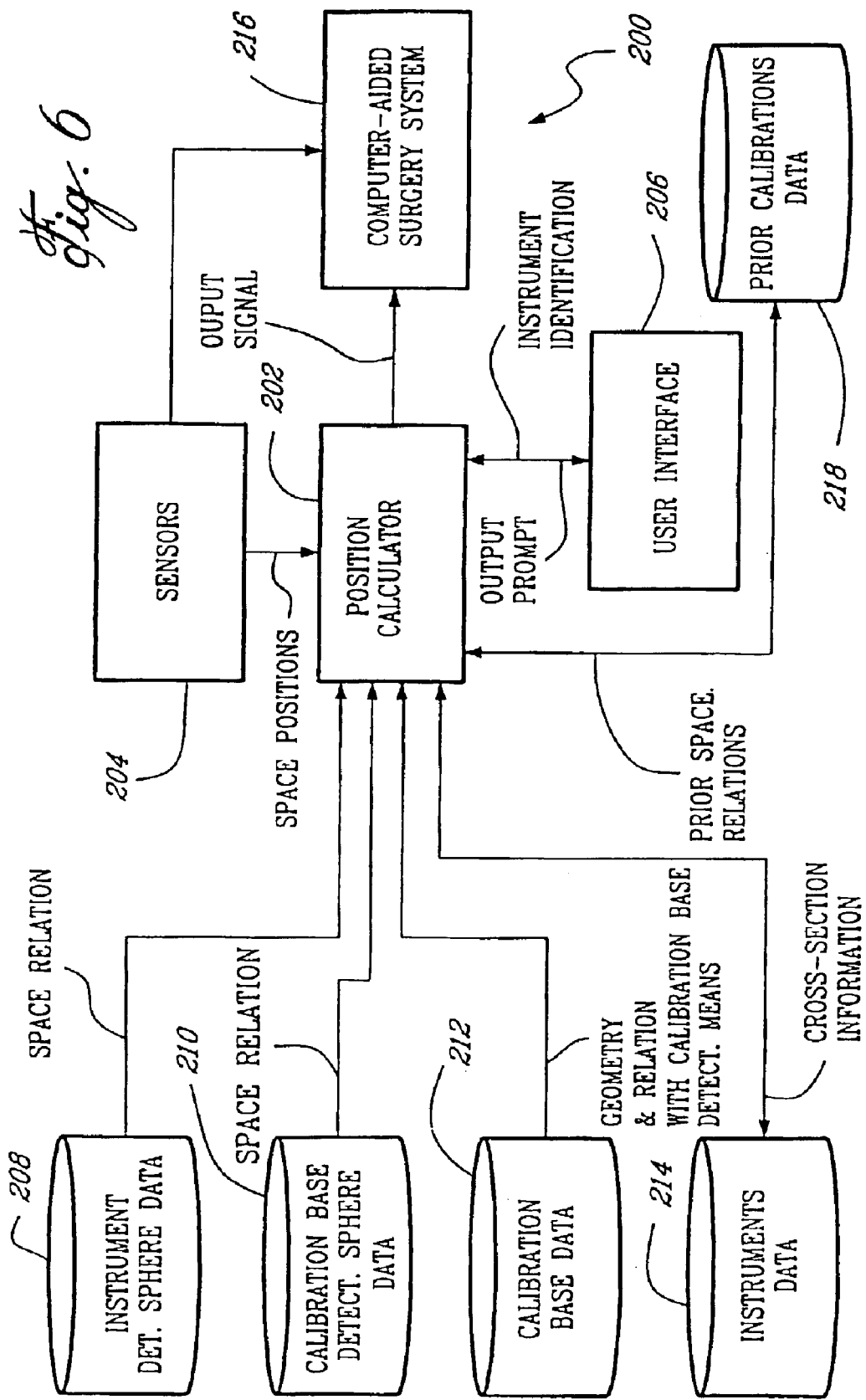
FIG. 6 is a block diagram illustrating a method of automatically calibrating surgical instruments in accordance with the present invention.

Referring now to FIG. 6, a positioning system for calibrating the surgical instrument S disposed in the calibration base C is generally shown at 200, and comprises a position calculator 202. The position calculator 202 is a computer program, which may be, for instance, installed on the computer-aided surgery platform. The position calculator 202 receives space locations, including the position and orientation, of the detectable spheres 44, 46 and 48 of the calibration base C, and the detectable spheres 110, 112 and 114 mounted on the surgical instrument S through sensors 204. The position calculator 202 also receives instrument identification from an operator through user interface 206. It is noted that the cross-sectional dimensions of instruments to be used with the position calculator 202 are stored thereby such as to be retrieved upon operator instrument identification. For instance, the operator may indicate that the instrument whose working tip is illustrated in one of FIGS. 3 to 5 is to be calibrated. In the event where the instrument information is not stored by the position calculator 202, it is possible for the operator to enter new information amongst the instrument data 214 through the user interface 206. The user interface 206 may comprise typical keyboard, mouse and monitor.

It is noted that the space relation 208 of the detectable spheres 110, 112 and 114 is stored by the position calculator 202, such that the latter will recognize them through the sensors 204. Other information stored by the position calculator 202 include the space relation 210 of the detectable spheres 44, 46 and 48, the space geometry 212 by the calibration base C, including the space relation between these spheres and the calibration base C. Also, the cross-section shapes and dimensions 214 of the various tools to be used is stored by the position calculator 202. Once the position and orientation of the detectable spheres 44, 46 and 48 and the detectable spheres 110, 112 and 114 are detected by the sensor 204, and the instrument is identified by the operator through the user interface 206, the position and orientation of the working tip 102 of this instrument is calculated with respect to the detectable spheres 110, 112 and 114 attached thereto, as explained above. This results in the calibration of the instrument, as prompted by the position calculator 202 to the user interface 206 and as signaled to the computer-aided surgery system 216.

The position calculator 202 also stores the prior calibration data 218, which consists in the calculated position and orientation of the tips of all the instruments which have been calibrated previously. This allows for a validation of the calibration of the instruments. For instance, the instrument S depicted in FIG. 1 is calibrated and used for surgery. The position calculator 202 will automatically store the position and orientation of the working tip 102 of the instrument S with respect to the position of the detectable spheres 110, 122 and 114 thereon. Thereafter, at the next calibration of the same instrument S, the position calculator 202 will compare the new calculated position and orientation of the working tip 102 to the stored reference position and orientation. If the new calculated position and orientation are not within an allowable range, the operator will be prompted to verify the state of the instrument and the positioning thereof in the calibration base C. If, after a second reading of the sensors 204 the position and orientation is the same as the previous one, the operator will be prompted to either accept the new space position and orientation, or to retry calibrating until the stored reference position and orientation are attained.

In the preferred embodiment, the calibration base C is constructed in accordance with high standards of precision such that the XY plane 14, the XZ plane 28 and the YZ plane 32 are all planar and in perpendicular relationship. Although other configurations are possible, the above described geometry of the calibration base C provides a simple solution.

The calibration base C is permanently calibrated as it does not change shape. As mentioned above, the calibration C is made of a material which can sustain great impacts (i.e. stainless steel). Also, as seen in FIG. 2, the first protrusion 22 and the second protrusion 24 are provided in order to protect the detectable spheres 44, 46 and 48 in case of a fall of the calibration base C.

Figure 7:
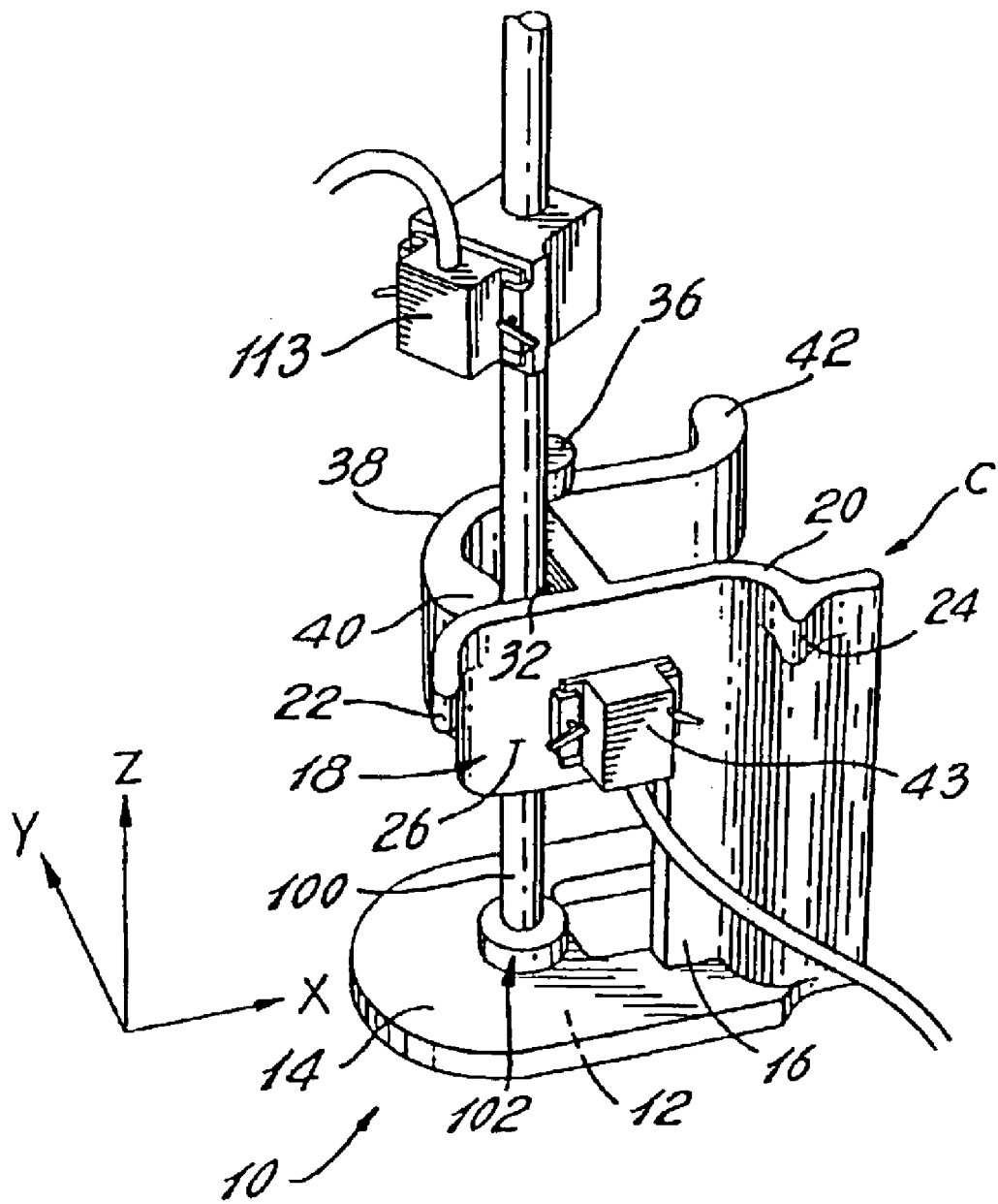
FIG. 7 is a perspective view of the automatic calibration unit with a tool in accordance with a further embodiment of the present invention.

Although the use of retro-reflective spheres has been described above, it is pointed out that the detection of the position and orientation of the instrument S and the calibration base C may be achieved by other devices such as magnetic sensors, ultrasound sensors and infrared LEDs. Referring to FIG. 7, a housing 43 is shown mounted to the calibration base C, whereas a housing 113 is shown secured to the surgical instrument S. The housings 43 and 113 may contain either magnetic sensors, ultrasound sensors or the like.

The use of the lever 38, for releasably securing the instrument S ensures the precise positioning of the latter with respect to the XZ plane 28 and the YZ plane 32 and is adapted for receiving shafts of various diameters (e.g. 3 to 37 mm) with its rounded end 40. It is pointed out that alternative mechanisms may be used instead of the spring-biased lever 38, so long as the working shaft is pressured against the planes 28 and 32. Gravity forces the tip 102 of the instrument S against the XY plane 14 in the preferred embodiment, thus rendering the above-described releasable connection virtually instantaneous.

The arm 106 of the surgical instrument S is of a material which is substantially less resistant to impacts than the blade 108. Therefore, in the event of a great impact on the surgical instrument S, the arm 106 would get deformed before the blade 108, thereby protecting the geometry thereof which defines the space positioning of the detectable spheres 110, 112 and 114 and is stored at 208 by the position calculator 102. Thus, if the arm 106 is damaged, the surgical instrument S may be quickly recalibrated according to the above described method in order to set the location of its tip 102 in space.

What is claimed is:

1. A calibration base to automatically calibrate any of a plurality of instruments having varying cross-sectional dimensions within a predetermined range for computer-aided surgery, each of the instrument, having a detectable portion, a working shaft and a tip at an end of the working shaft, said calibration base comprising;

first detectable means secured thereto for detecting a position and an orientation thereof in space by sensor means connected to a position calculator; and said calibration base adapted to receive and to releasably secure the working shaft of any of the instruments and providing a first abutting surface for the tip thereof in such a way that a position and orientation of the tip of any of the instruments secured therein is calculable when working shaft cross-section dimensions thereof are known;

whereby any of the instruments is calibrated when the position and orientation of the tip of the working shaft thereof is calculated.

2. The calibration base as defined in claim 1, wherein the first abutting surface extends in a direction generally opposed to a longitudinal axis of the working shaft of any one of the instruments.

3. The calibration base as defined in claim 2, wherein the working shaft of any of the instruments is abutted against a second and a third abutting surface.

4. The calibration base as defined in claim 3, wherein said second, and said third abutting surfaces define a V-shaped channel.

5. The calibration base as defined in claim 4, wherein said first, second end third abutting surfaces are each in a perpendicular relation with respect one to another.

6. The calibration base as defined claim 1, wherein the working shaft of any one of the instruments is releasably secured against abutting surfaces of said calibration bass by a biasing member.

7. The calibration base as defined in claim 6, wherein said biasing member comprises a spring-loaded lever.

8. The calibration base as defined in claim 7, wherein said lever has a generally rounded end surface for engaging contact with the working shaft.

9. The calibration base as defined in claim 1, wherein said first detectable means comprises three optically detectable spheres.

10. The calibration base as defined in claim 9, wherein each said detectable sphere is retro-reflective.

11. The calibration base as defined in claim 9, wherein said detectable spheres are detachable from said calibration base.

12. The calibration base as defined in claim 1, wherein said first detectable means are disposed in a concavity of said calibration base for impact protection thereof.

13. The calibration base as defined in claim 12, wherein said concavity is comprised of at least a pair of protrusions.

14. A method for calibrating any of a plurality of instruments having varying cross-sectional dimensions within a predetermined range with a position calculator connected to sensor means for computer-aided surgery, any one of the instruments having first detectable means being secured thereto and being releasably secured for calibration in a calibration base having second detectable means, said method comprising the steps of:
   (i) detecting a position and orientation in space of said first and second detectable means by said sensor means;
   (ii) receiving instrument data; and
   (iii) calculating a position and orientation of a tip of any one of the instruments secured in said calibration base with respect to said second detectable means as a function of said instrument data whereby the instrument is calibrated with respect to said first detectable means.

15. The method as defined in claim 14, wherein the step (ii) includes receiving said instrument data from an operator through a user interface.

16. The method as defined in claim 14, wherein the step (iii) includes comparing the calculated position and orientation with a stored reference position and orientation of the tip of a same instrument as calculated in a previous calibration of the same instrument.

17. The method as defined in claim 16, wherein the step (iii) includes prompting an operator to verify the instrument if the calculated position and orientation is outside tolerances of the position and orientation of the previous calibration of the same instrument and waiting for an operator signal to proceed with a subsequent calibration calculation.

18. The method as defined in claim 17, wherein the step (iii) is repeated until the position and orientation of the previous calibration of the same instrument within said tolerances is attained.

19. The method according to claim 18, wherein the step (iii) includes asking the operator about setting a same position and orientation as calculated by at least two subsequent calibration calculation as a new accepted calibration calculation.

20. The method as defined in claim 15, wherein said instrument data includes one of identification data relating to instrument cross sectional dimension data stored by said position calculator and of instrument cross-sectional dimension data to be stored by said position calculator for subsequent calibrations.

21. A position calculator computer program product comprising code means recorded in a computer readable memory for executing a method for calibrating any of a plurality of instruments having varying cross-sectional dimensions within a predetermined range with a position calculator connected to sensor means for computer-aided surgery, any one of the instruments having first detectable means being secured thereto and being releasably secured for calibration in a calibration base having second detectable means, said method comprising the steps of:
   (i) detecting a position and orientation in space of said first and second detectable means by said sensor means;
   (ii) receiving instrument data; and
   (iii) calculating a position and orientation of a tip of any one of the instruments secured in said calibration base with respect to said second detectable means as a function of said instrument data whereby the instrument is calibrated with respect to said first detectable means.

22. A System for automatic calibration of instruments for computer-aided surgery, comprising:
   a calibration base to automatically calibrate any of a plurality of instruments having varying cross-sectional dimensions within a predetermined range for computer-aided surgery, each of the instruments having a detectable portion, a working shaft and a tip at an end of the working shaft, said calibration base comprising first detectable means secured thereto for detecting a position and an orientation thereof in space by sensor means connected to a position calculator, and said calibration base adapted to receive and to releasably secure the working shaft of any of the instruments and providing a first abutting surface for the tip thereof in such a way that a position and orientation of the tip of any of the instruments secured therein is calculable when working shaft cross-section dimensions thereof are known, whereby any of the instruments is calibrated when the position and orientation of the tip of the working shaft thereof is calculated;
   said detectable portion on the instruments comprising second detectable means for space positioning of the instruments, said second detectable means being adapted to be secured to any of the instruments;
   said sensor means for detecting a position and orientation in space of said first and second detectable means; and
   a position calculator connected to said sensor means for calculating a position and orientation of the tip of the working shaft of any of the instruments secured in said calibration base with respect to the first detectable means according to a method comprising the steps of (i) detecting a position and orientation in space of said first and second detectable means by said sensor means, (ii) receiving instrument data, and (iii) calculating a position and orientation of a tip of any one of the instruments secured in said calibration base with respect to said first detectable means as a function of said instrument data;
   whereby any of the instruments is calibrated with respect to said second detectable means when the position and orientation of the tip of the working shaft thereof is calculated.

23. The system as claimed in claim 22, wherein said second detectable means comprises three other optically detectable spheres.

24. The system as claimed in claim 23, wherein each said other detectable sphere is retro-reflective.

25. A method for calibrating instruments with a position calculator connected to sensor mean for computer-aided surgery, the instruments having detectable means being secured thereto, said method comprising the steps of:
   (i) detecting a position and orientation in space of said detectable means by the sensor means;

(ii) calculating a position and orientation of a predetermined portion of any one of the instruments with respect to said detectable means; and (iii) comparing the calculated position and orientation with a stored reference position and orientation of the predetermined portion of a same instrument as calculated in a previous calibration of the same instrument, and prompting an operator to verify the instrument if the calculated position and orientation is outside tolerances of the position and orientation of the previous calibration of the same instrument and waiting for an operator signal before repeating the steps (i), (ii) and (iii), whereby the instrument calibration is validated if the calculated position and orientation is within tolerances of the position and, orientation of the previous calibration of the same instrument.

26. The method as defined in claim 25, wherein the step (iii) is repeated until the position and orientation of the previous calibration of the same instrument within said tolerances is attained.

27. The method as defined in claim 26, wherein the step (iii) includes asking the operator about setting a same position and orientation as calculated by at least two subsequent calibration calculation as a new accepted calibration calculation.

28. The method as defined in claim 25, wherein the step (iii) includes accepting instrument identification data from a user, storing the position and orientation from the previous calibration in association with the identification data and requesting the user to identify the instrument prior to the steps (i), (ii) and (iii).

29. A position calculator computer program product comprising code means recorded in a computer readable memory for executing a method for calibrating instruments with a position calculator connected to sensor means for computer-aided surgery, the instruments having detectable means being secured thereto, said method comprising the steps of:

(i) detecting a position and orientation in space of said detectable means by the sensor means, (ii) calculating a position and orientation of a predetermined portion of any of one of the instruments with respect to said detectable means; and (iii) comparing the calculated position and orientation with a stored reference position and orientation of the predetermined portion of a same instrument as calculated in a previous calibration of the name instrument, and prompting an operator to verify the instrument if the calculated position and orientation is outside tolerances of the position and orientation of the previous calibration of the name instrument and waiting for an operator signal before repeating the steps (i), (ii) and (iii);

whereby the instrument calibration is validated if the calculated position and orientation is within tolerances of the position and orientation of the previous calibration of the same instrument.

* * * * *